United States Patent [19]

Ross

[11] 4,023,909

[45] May 17, 1977

[54] NULL BALANCE ALPHAMETER

[75] Inventor: Charles C. Ross, San Diego, Calif.

[73] Assignee: The United States of America as represented by the Secretary of the Navy, Washington, D.C.

[22] Filed: Jan. 15, 1976

[21] Appl. No.: 649,435

[52] U.S. Cl. .............................. 356/205; 250/575; 356/183; 356/208; 356/246

[51] Int. Cl.$^2$ ................. G01N 21/22; G01N 21/26

[58] Field of Search .............. 356/73, 89, 183, 205, 356/206, 207, 208, 246; 250/575

[56] References Cited

UNITED STATES PATENTS

| | | | |
|---|---|---|---|
| 2,035,649 | 3/1936 | Goudsmit et al. ................. | 356/183 |
| 2,528,924 | 11/1950 | Vassy ................................. | 356/205 |
| 3,976,369 | 8/1976 | McCardell et al. ................ | 356/208 |

Primary Examiner—Vincent P. McGraw

Attorney, Agent, or Firm—Richard S. Sciascia; Ervin F. Johnston; Thomas Glenn Keough

[57] ABSTRACT

An alphameter provides an indication of the volume absorption coefficient and the small angle forward scattering coefficient to give an indication of underwater visibility. A laser beam is alternately pulsed through the surrounding water and a reference fluid which fills a telescoping chamber. A photodiode is illuminated by the alternating pulses and representative signals are fed to a feedback loop where a comparison is made with signals emanating from the laser. If the representative signals exceed or fall below the predetermined threshold range, a DC motor enlarges or lessens the interior volume of the telescoping chamber causing more or less of the reference fluid to be contained therein. When the representative signals fall within the predetermined threshold range the telescoping chamber is no longer displaced and a readout indicates what the transmissivity of the surrounding water is.

10 Claims, 3 Drawing Figures

NULL BALANCE ALPHAMETER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Marine scientists and photographers often need to know the transmissivity of the surrounding water, since knowing exactly what the underwater water visibility is is a parameter to be considered during many experiments. That which affects underwater visibility includes, among several things, the volume absorption coefficient $a$, and the small angle forward scattering coefficient $s$. These generally are identified as the transmissivity factor $m$, where:

$$m = e^{-(a+s)R} \qquad (1)$$

where
 $m$ = transmissivity
 $R$ = path length.
Alpha is defined as $$\alpha = a + s \qquad (2)$$
$$= (-1/R)\ln m \qquad (3)$$

and has the standard unit of meter $^{-1}$. Alphameters measure this parameter, and are used for such tasks as comparing the performance of optical systems under different water conditions, video processing to compensate for range variations, taking data for visibility prediction studies, and analysis of liquid solutions other than water.

Current methods of constructing alphameters generally use a stable light source and a photodetector whose output voltage or current is a linear function of light intensity, and, therefore, transmissivity. A logarithmic amplifier, or digital processing is used to determine $\alpha$.

A null balance transmissometer has been described that develops an error voltage which drives a circular linear gradient neutral density filter in an optical path to null the error voltage. The angular position of the filter is proportional to the transmissivity. Disadvantages of this device are the difficulty of manufacturing an accurate linear gradient neutral density filter, and the processing required to obtain alpha.

SUMMARY OF THE INVENTION

The present invention is directed to providing an apparatus for comparing the absorption and scattering of light in a sample fluid with respect to a reference fluid. A means for radiating a beam of light illuminates a means for generating representative beam signals. Also provided is a means for splitting the light beam into additional first and second parallel components. The first parallel component is passed through the sample fluid and the second parallel component is transmitted through the reference fluid. In line with the parallel first and second component beams, a means transforms the components into first and second component signals. A comparing means receives the first and second component signals and a means changes the dimensions of the transmitting means when predetermined amplitude variations among the beam signals and the first and second component signals are detected by the comparing means.

It is an object of the invention to provide an improved alphameter.

Another object of the invention is to provide an alphameter giving a readout directly proportional to alpha and which avoids the error and complexity of logarithmic amplifiers or the time and expense of digital processing.

Still another object is to provide an alphameter employing a null balance technique independent of photodetector linearity and light source intensity.

Still another object is to provide an optical balancing element fabricated from components already well known in the state-of-the-art.

Yet another object is to provide an optical balancing element capable of being used with a variety of fluids of known optical properties to fit a given situation.

A further object is to provide an alphameter of potentially high resolution having a potentially high accuracy.

Still another object is to provide a device that automatically pressure compensates itself and is capable of being used at any orientation.

Another object of the invention is to provide an alphameter responsive to parallel beams of light which compares amplitude variations to result in a visual readout.

These and other objects of the invention will become more readily apparent from the ensuing description when taken together with the drawings.

DESCRIPTION OF THE PREFERRED EMBODIMENT

Figure 1:
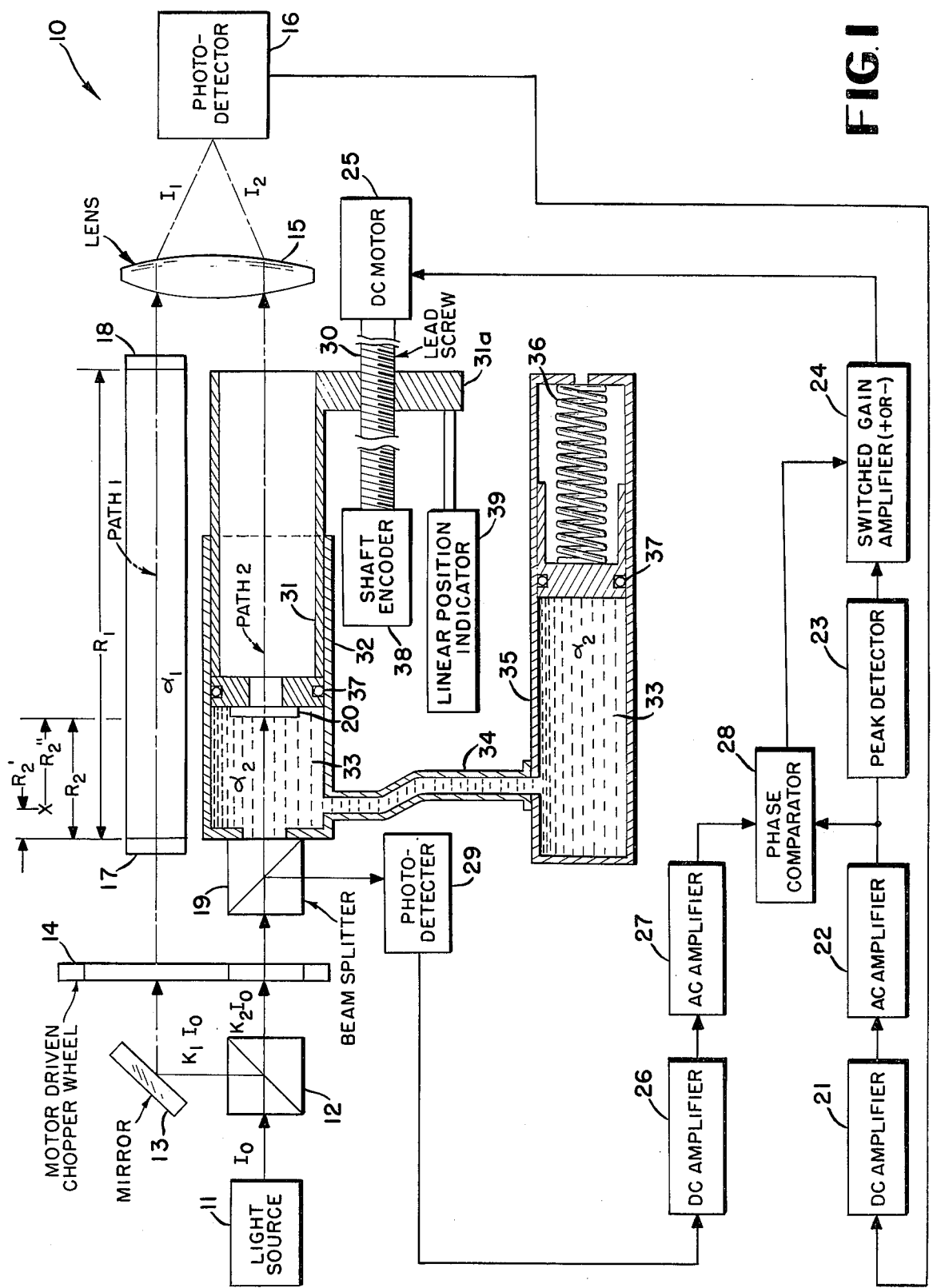
FIG. 1 is a schematical representation of a preferred embodiment of the invention.
Figure 2:
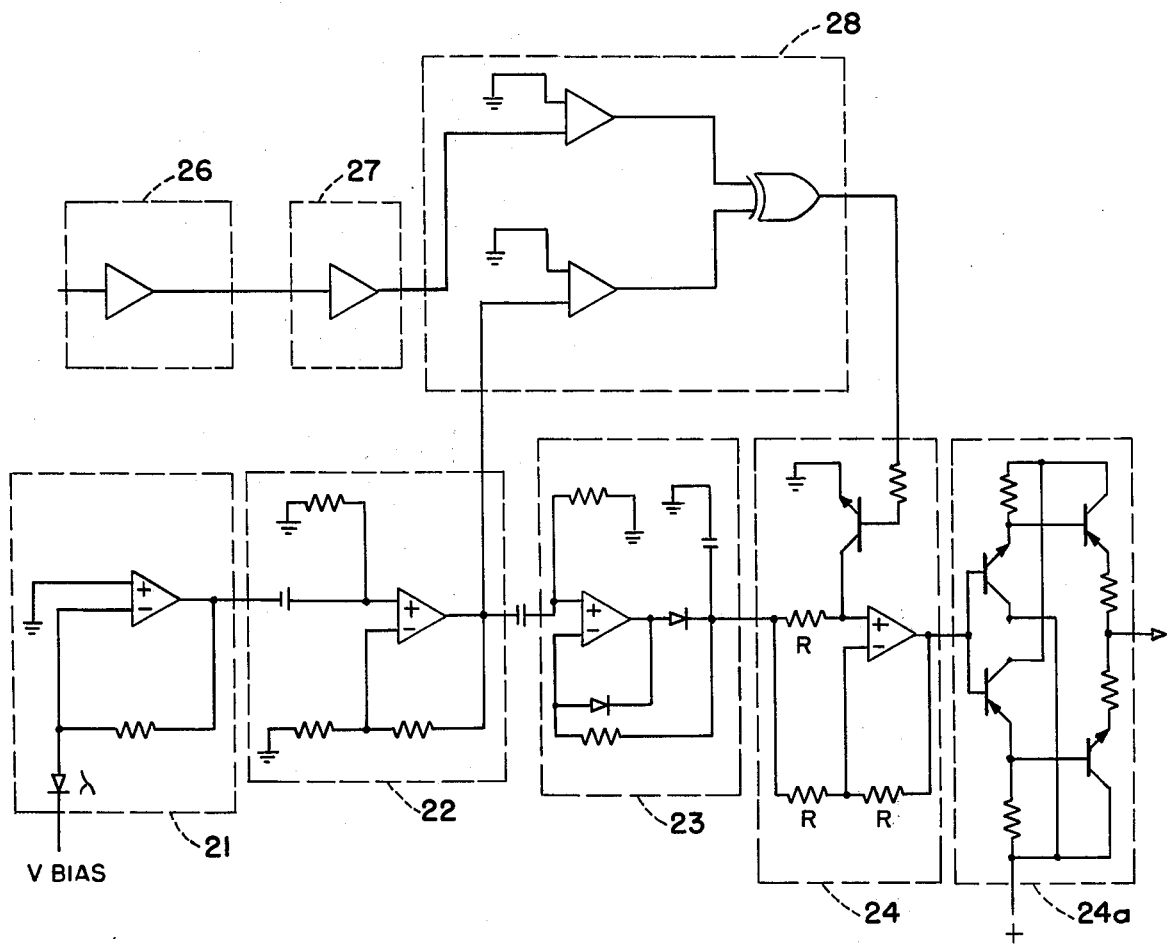
FIG. 2 is a representative circuit diagram of the feedback loop used for nulling.

Referring now to the drawings, a representative embodiment of the null balanced alphameter 10 is schematically depicted. A laser, or other well collimated light source 11 directs a beam at an intensity $I_0$ toward a beam splitter 12 which splits the $I_0$ beam into two beams having intensities $k_1 I_0$ and $k_2 I_0$. A mirror 13 redirects the first beam to orient it parallel to the second beam and both beams pass through a motor driven chopper wheel 14. The cogs and spaces of the chopper wheel are as wide as the separation of the two beams at their point of incidence on the wheel. The arrangement of the cogs and spaces are such as to block the passage of one beam while the other passes through and to alternate the passage of the two beams. Thusly, the beams are gated alternately in a path 1 and a path 2 onto the surface of a lens 15, which converges them onto a photo detector 16.

Path 1 traverses a fixed path length having a dimension $R_1$ lying between a pair of transparent windows 17 and 18. Between these windows a fluid, for example, ambient seawater, is enclosed which has an unknown alpha, $\alpha_1$. The intensity $I_1$ at detector 16 which travels along path 1 is expressed:

$$I_1 = C_1 k_1 I_0 e^{-\alpha_1 R_1} \qquad (4)$$

where
$C_1$ = optical path transmissivity, exclusive of the fluid in path 1 having a length $R_1$, from light source 11 to photodetector 16.

The second beam in path 2 passes through a second beam splitter 19 into the reference fluid having a known alpha, $\alpha_2$. The chamber containing the reference fluid has a variable path length $R_2$ and the second beam passes through a transparent window 20. From there the beam impinges on lens 15 and to the photodetector 16 where its intensity $I_2$ is expressed as:

$$I_2 = C_2 k_2 I_o e^{-\alpha_2 R_2} \qquad (5)$$

where
$C_2$ = optical transmissivity of path 2 exclusive of the fluid in path 2 having the length $R_2$ from light source 11 to photodetector 16.

When a nulled condition exists in the alphameter,
$$I_1 = I_2 \qquad (6)$$

and $$R_2 = \frac{\alpha_1 R_1}{\alpha_2} - \frac{-1}{\alpha_2} \ln \frac{(C_2 k_2)}{C_1 k_1} \qquad (7)$$

However, if $$C_1 k_1 = C_2 k_2 \qquad (8)$$

then $$R_2 = \frac{R_1}{\alpha_2} \cdot \alpha_1 \qquad (9)$$

From the foregoing analysis it becomes apparent that the length $R_2$ of the reference fluid $\alpha_2$ is a linear function of $\alpha_1$, since the length $R_1$ and the properties of $\alpha_2$ are known constants.

The condition of having intensity $I_1$ equal to the intensity $I_2$ is easily maintained by a feedback loop which nulls the AC content of the electrical output signal from detector 16. However, DC amplifiers 21 and 26 are normally required when using PIN photodiodes for detectors 16 and 29.

The output amplitude of AC amplifier 22 is a measure of the error between intensity $I_1$ and intensity $I_2$ which peak detector 23 converts to a DC signal. This DC signal drives the switched gain amplifier 24 and its associated current amplifier 24a. The resultant signal is fed to drive the motor 25.

Which way the motor rotates or applies its driving force is dependent upon the output of an AC amplifier 27. The amplifier receives a reference signal from a phase detector 29 which was reflected to the detector via beam splitter 19. An error signal, that being the signal generated when $I_1$ does not equal $I_2$ is compared in phase in phase comparator or detector 28. The detector determines the gain polarity (plus or minus) which is fed to switch gain amplifier 24.

In response to a positive or negative resultant signal fed to the DC motor 25, it rotates an interconnected lead screw 30. This rotational motion moves an inner cylinder 31 in or out of an outer cylinder 32 changing the length $R_2$ of path 2. The chamber in path 2 is filled with the reference fluid 33 as well as a tube 34 and a reservoir 35. The telescoping cylinders draw in or expell the reference fluid in response to the changing dimensions of the chamber.

Another feature of this arrangement renders this device insensitive to ambient pressure variations as well as to changes of its orientation. A spring 36 and a pair of O-rings 37 maintain a greater than ambient pressure on the reference fluid to prevent influx and possible contamination, to take up any backlash in the lead screw 30 and to permit the use of the alphameter at any orientation or depth.

The reading of the alpha of the sample fluid $\alpha_1$ can readily be obtained by noting the readout on a preprogrammed shaft recorder 38 or a linear position indicator 39. Both of these well known devices are preprogrammed to give representative readings of an unknown $\alpha_1$ when internal cylinder 31 has been axially displaced to a predetermined position. At this one position the condition $I_1$ equals $I_2$ exists and there is nulling in the feedback loop.

The disclosed alphameter possesses a great deal of flexibility to allow its using a variety of reference fluids that have widely varying optical properties. The condition of $C_1 k_1$ not being equal to $C_2 k_2$ may be established by constructing the alphameter with $C_1 k_1$ being greater than $C_2 k_2$. This permits the device to be preset by as much as having $\alpha_1$ equal to zero (the path $R_1$ being through air, for example). Now, when the servo loop nulls, the length $R_2$ of path 2 will not be zero but the shaft encoder 38 or the linear position indicator 39 may be set to indicate zero. This changes the optical constant $C_2$ to include a fixed part $R_2'$ of path $R_2$ such that $$C_2' = C_2 + e^{-\alpha_2 R_2'} \qquad (10)$$

and changes the measured parameter to be $$R_2'' = R_2 - R_2' \qquad (11)$$

$$= \frac{\alpha_1 R_1}{\alpha_2} - \frac{1}{\alpha_2} \ln \frac{C_2' k_2}{C_1 k_1} - R_2' \qquad (12)$$

$$= \frac{R_1}{\alpha_2} \cdot \alpha_1 \qquad (13)$$

Now, the fluid causing nulling of the feedback loop, when $I_1$ equals $I_2$, is air. It is obvious that the same alphameter that determined alpha for seawater has been easily modified to determine the alpha for air, thusly giving its great flexibility for a wide variety of uses.

Figure 3:
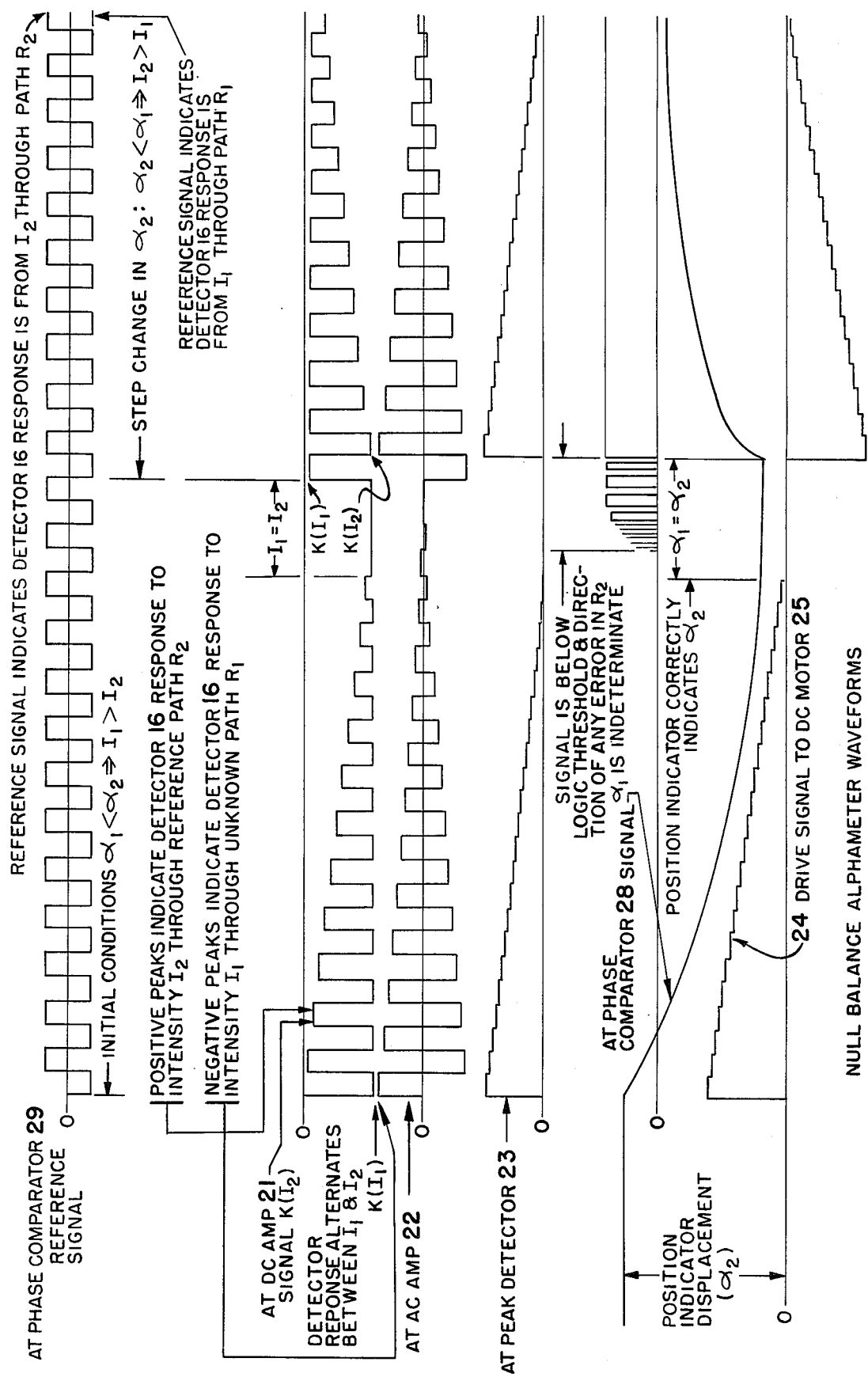
FIG. 3 is a graph showing the signals in the feedback loop on an identical time basis.

A more thorough understanding of the circuit's operation may be had by noting FIG. 3 along with the other figures of the drawings. In the first instance portrayed to the left, $\alpha_1$ is less than $\alpha_2$ and, therefore, $I_1$ is much greater than $I_2$. The waveform of the reference signal in phase comparator 29 is fed to phase comparator 28. Simultaneously, $I_1$ and $I_2$ from photo detector 16 are fed to DC amplifier 21. It is noted that the $I_2$ signal has a much greater value than the $I_1$ signal. This causes the output of AC amplifier 22 to fluctuate a pure AC signal since the coupling capacitor between the stages blocks the DC component of $I_1$ and $I_2$. At peak detector 23 this AC signal is smoothed out and the phase comparator signal also decays.

An exclusive-or circuit in the phase comparator triggers the switched gain amplifier 24 to pass a driving signal to the DC motor 25 via a current amplifier 24a. The motor is driven to displace inner cylinder 31 until $I_1$ equals $I_2$ and the value of $\alpha_1$ is indicated on the shaft encoder 38 or linear position indicator 39.

To the right side of FIG. 3, the triggering potentials are shown for the case when $\alpha_2$ is less than $\alpha_1$ and $I_2$ is greater than $I_1$. Substantially the same process follows to make $I_2$ equal to $I_1$ and the resultant nullifying of the circuit.

Obviously, many modifications and variations are possible in the light of the above teachings, and, it is therefore understood the invention may be practiced otherwise than as specifically described.

What is claimed is:

1. An apparatus for comparing the absorption and scattering of light in a sample fluid with respect to a reference fluid comprising:
    means for radiating a beam of light;
    means disposed to receive the light beam for generating representative beam signals;
    means also disposed to receive the light beam for splitting the light beam into additional first and second parallel components;
    means disposed to receive the first parallel component for passing it through the sample fluid;
    means disposed to receive the second parallel component for transmitting it through the reference fluid;
    means disposed to receive the first and second components from the passing means and the transmitting means for transforming the components into first and second component signals;
    means coupled to the generating means and the transforming means for comparing the beam signals and the first and second component signals;
    means coupled to the comparing means for changing the dimension of the transmitting means when predetermined amplitude variations among the beam signals and the first and second component signals are detected by the comparing means; and
    means connected to the transmitting means for indicating the absorption and scattering of light in the sample fluid when the transmitting means stops changing dimensions.

2. An apparatus according to claim 1 further including:
    means coupled to the transmitting means for feeding greater and lesser amounts of the reference fluid to the transmitting means in response to dimensional changes by the changing means.

3. An apparatus according to claim 2 further including:
    means interposed in the light beam for sequentially alternately interrupting the first and second parallel components of the light beam.

4. An apparatus according to claim 3 further including:
    means disposed adjacent the passing means and transmitting means for focusing the first and second components of the light beam onto the transforming means.

5. An apparatus for comparing the absorption and scattering of light in a sample fluid with respect to a reference fluid comprising:
    means for radiating a beam of light;
    means disposed to receive the light beam for generating representative beam signals;
    means also disposed to receive the light beam for splitting the light beam into additional first and second parallel components;
    means disposed to receive the first parallel component for passing it through the sample fluid;
    means disposed to receive the second parallel component for transmitting it through the reference fluid, the transmitting means includes a pair of telescoping sections of tubing cooperating to change the length of an internal chamber and thereby change the distance one of the parallel components must travel through the reference fluid;
    means disposed to receive the first and second components from the passing means and the transmitting means for transforming the components into first and second component signals;
    means coupled to the generating means and the transforming means for comparing the beam signals and the first and second component signals;
    means coupled to the comparing means for changing the dimension of the transmitting means when predetermined amplitude variations among the beam signals and the first and second component signals are detected by the comparing means;
    means connected to the transmitting means for indicating the absorption and scattering of light in the sample fluid when the transmitting means stops changing dimensions;
    means coupled to the transmitting means for feeding greater and lesser amounts of the reference fluid to the transmitting means in response to dimensional changes by the changing means;
    means interposed in the light beam for sequentially alternately interrupting the first and second parallel components of the light beam; and
    means disposed adjacent the passing means and transmitting means for focusing the first and second components of the light beam onto the transforming means.

6. An apparatus according to claim 5 in which the feeding means is a spring biased and sealed reservoir of reference fluid rendering it insensitive to ambient pressure variations.

7. An apparatus according to claim 6 in which the generating means and the transforming means are photo detectors coupling signals to the comparator circuit.

8. An apparatus according to claim 7 in which the splitting means is a pair of beam splitters optically cooperating with a mirror to create the first and second parallel components and ensure the generation of the beam signals.

9. An apparatus according to claim 8 in which the comparing means includes a phase comparator coupled to a switched gain amplifier.

10. An apparatus according to claim 9 in which the changing means is motor-gear arrangement engaging one of the tubing sections.

* * * * *